United States Patent [19]
Lopez

[11] Patent Number: 5,193,574
[45] Date of Patent: Mar. 16, 1993

[54] PROTECTIVE STRUCTURE FOR CONNECTION SITE FOR MEDICAL USE

[75] Inventor: Georges A. Lopez, Craponne, France

[73] Assignee: Laboratoire Cair L.G.L., Tarare, France

[21] Appl. No.: 876,432

[22] Filed: Apr. 30, 1992

[51] Int. Cl.$^5$ ............................................. F16K 37/28
[52] U.S. Cl. .................................. 137/382; 137/343; 137/377; 604/905
[58] Field of Search ...................... 137/343, 377, 382; 285/45, 55; 604/905

[56] References Cited

U.S. PATENT DOCUMENTS

| | | | |
|---|---|---|---|
| 4,301,828 | 11/1981 | Martin, Jr. ............................ | 137/382 |
| 4,422,314 | 12/1983 | Cooper ................................. | 137/382 |
| 4,473,369 | 9/1984 | Lueders et al. ...................... | 604/905 |
| 4,655,762 | 4/1987 | Rogers ................................. | 604/905 |
| 4,804,012 | 2/1989 | Goldman et al. .................... | 137/343 |
| 4,896,465 | 1/1990 | Rhodes et al. ...................... | 248/74.2 |
| 4,950,230 | 8/1990 | Kendell ................................ | 604/32 |

FOREIGN PATENT DOCUMENTS

| | | |
|---|---|---|
| 0073432 | 3/1983 | European Pat. Off. . |
| 0336853 | 10/1989 | European Pat. Off. . |
| 2617717 | 1/1989 | France . |

Primary Examiner—A. Michael Chambers
Attorney, Agent, or Firm—Oliff & Berridge

[57] ABSTRACT

Protective structure for a connection site for medical use, including connection sites having at least one valve (3) integral with an attachment panel, and a housing slidably mounted on the panel including two half-shells made of synthetic material. The half-shells are at lengthwise rear walls, provided on lengthwise front walls with elastic closing means and provided with foam padding, having depressions for fitting valves and tubes of the connection site.

According to the invention the half-shells are articulated by independent, spaced hinges on thin, lengthwise edges of a rear transverse wall integral with a slide and movably mounted on the panel. The length of the panel is at least equal to a distance that the slide must travel to achieve total clearance of the connection site by the two half-shells in an open position.

3 Claims, 2 Drawing Sheets

PROTECTIVE STRUCTURE FOR CONNECTION SITE FOR MEDICAL USE

BACKGROUND OF THE INVENTION

Numerous medical fluids, both drugs and nutrient solutions, are administered to patients parenterally. The patient is generally fitted with a catheter inserted into a vein, connected in turn to a fluid supply tube. In order to adjust the treatment to the patient's status at any moment in time, it is necessary to be able to inject several fluids simultaneously or alternately. For this purpose, at the end opposite the catheter end, a line is equipped with a site for connecting several tubes, having a three-way valve or a valve manifold.

To avoid the risk of contaminating the patient, it is necessary to keep this site sterile.

For this purpose, protection by means of a housing made of synthetic material having two articulated half-shells each padded with foam designed to be soaked with an antiseptic agent is known. The walls of the housing have openings for tubes to pass therethrough and are equipped with elastic closing means.

In general, in a wall opposite that provided with the closing means, the housing has a slot for passage of a panel integral with the connection site serving to attach the latter to a fixed support disposed on a stand. At the present time this attachment is provided by a clamp which passes through a hole provided in one of the half-shells of the housing to grip the panel and renders this half-shell practically integral with the valve manifold of the connection site and impedes the opening movements of the other half-shell. As a result, with the present structure, it is difficult and sometimes even impossible to manipulate the valves. Moreover, they can injure personnel responsible for activating the valves, something which counteracts, the desired asepsis.

SUMMARY OF THE INVENTION

The goal of the present invention is to remedy this situation by providing a protective structure which allows easy access to any of the valves in the manifold without thereby affecting asepsis.

For this purpose, in the structure according to the invention, the half-shells are articulated by independent, spaced hinges on thin, lengthwise edges of a rear transverse wall, this wall being integral with a slide movably mounted on the panel connected to the connection site, with the length of this panel being at least equal to the distance the aforementioned slide must travel to obtain total clearance of the protection site by the two open half-shells.

Thus, when the caregiver wishes to access any of the valves, as soon as he has activated the elastic closing means of the two half-shells in the unlocking direction, he can at the same time slide these two half-shells in the direction of the attachment clamp to clear the connection site totally. As a result, access to the connection site is facilitated and any risk of injury is eliminated. After adjustment of the valves, the two half-shells of the manifold need only be brought together and closed on this manifold for resumption of the desired sterile conditions.

In one embodiment of the invention, the two half-shells of the housing are connected to spring means which, when the housing is opened, are able to move the two half-shells on the panel in the direction of the rear end of this panel.

In this way, as soon as the operator has activated the closing means in the unlocking direction, the spring means themselves move the half-shells to release the valve manifold.

Other characteristics and advantages will emerge from the following description with reference to the attached schematic drawing which shows two embodiments of this structure as a nonlimiting example.

DETAILED DESCRIPTION OF PREFERRED EMBODIMENTS

Figure 1:
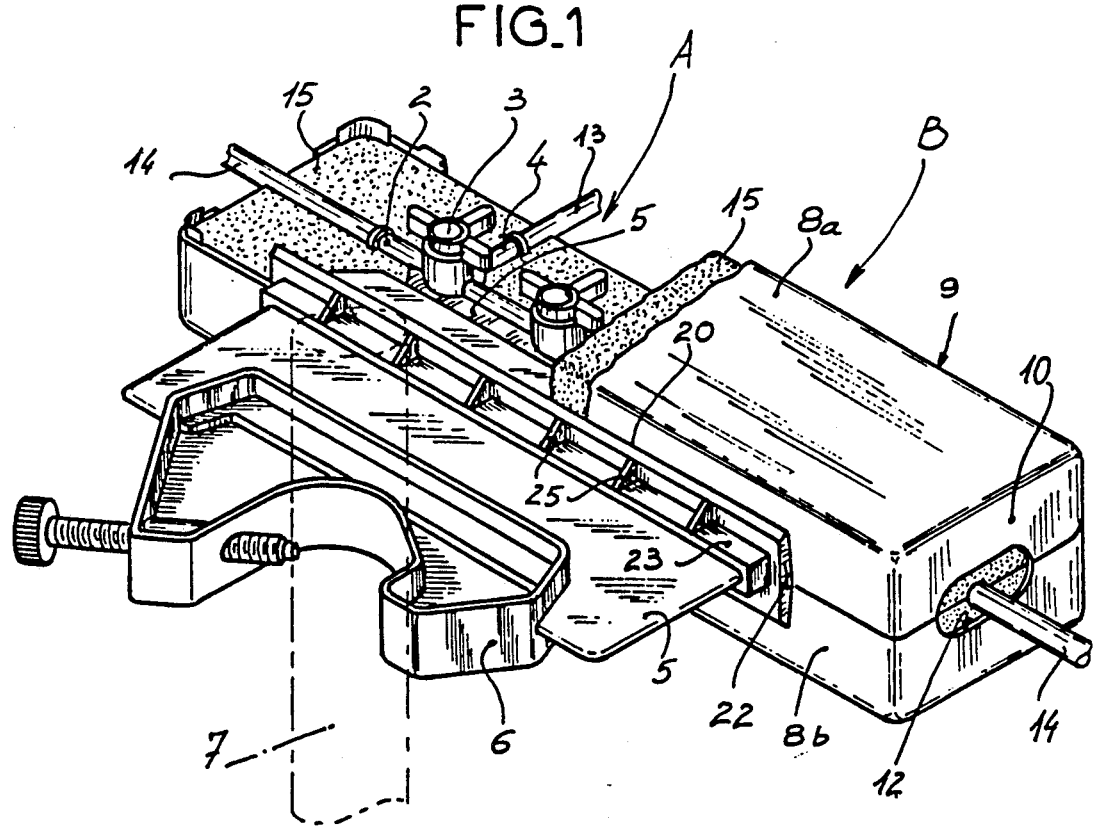
FIG. 1 is a perspective view with a partial cross-section of the upper half-shell of a first embodiment of a protective structure according to the invention.

In the figures, A designates a connection site comprising a main tube 2 which passes through the body in a straight line and several valves 3, each of which has a transverse tube 4. Tube 2 is integral with one of the ends of a panel 5 whose other end is integral with a clamp for attachment to the riser 7 of a stand or a bed. This protection site is protected by a housing designated in general by B, composed of two half-shells 8a and 8b. Each of these half-shells has, in its front wall 9 and its end walls 10, openings 12 for passage of flexible tubes 13 and 14 which connect to tubes 4 and 2. Finally, each half-shell is padded with a foam 15 made of synthetic material which has depressions 15a to accommodate the elements of the site. The material is designed to be soaked with an antiseptic agent. The closure of the two housing elements 8a and 8b is locked by a closing system located on the front walls and shown in FIGS. 2 and 3. This closing system comprises fingers 16 and levers 17 with elastic articulation 18.

According to the invention, half-shells 8a and 8b are not articulated directly with each other by a single hinge as is usual, but by two thin, lengthwise edges 20, which form hinges of an additional transverse rear wall 22 integral with a slide 23. Slide 23 is traversed by a hole 24 which allows it to move freely on panel 5 integral with connection site A.

FIG. 1 shows that, to confer rigidity on the hinges thus constituted, and to guarantee proper closure of the two half-housings, the connection between wall 22 and slide 23 is reinforced by gussets 25.

Figure 3:
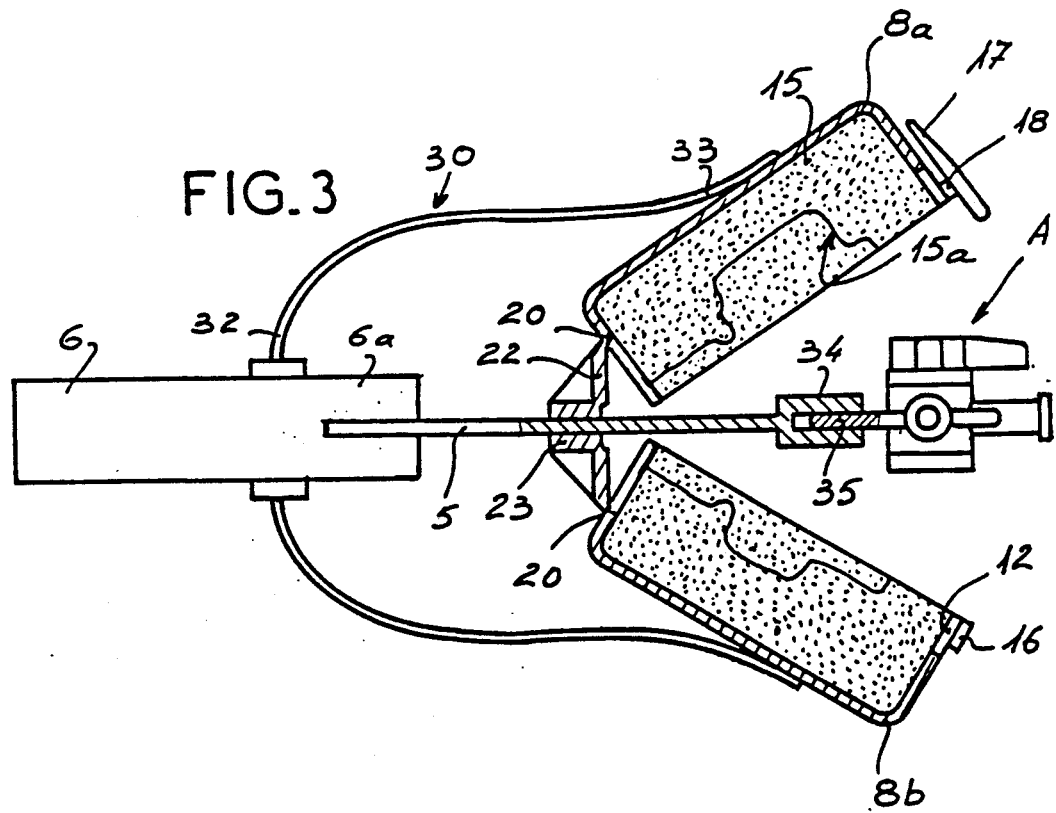

Because of this arrangement, as shown in FIG. 3, when the operator activates locking means 16-17 of the two half-shells 8a-8b to proceed with opening in order to access connection site A, it is very easy, by maintaining pressure on either of the two half-shells, to slide these two half-shells together over panel 5 a length at least equal to the distance C that the slide must travel to achieve total clearance by the two half-shells of connection site A.

Figure 2:
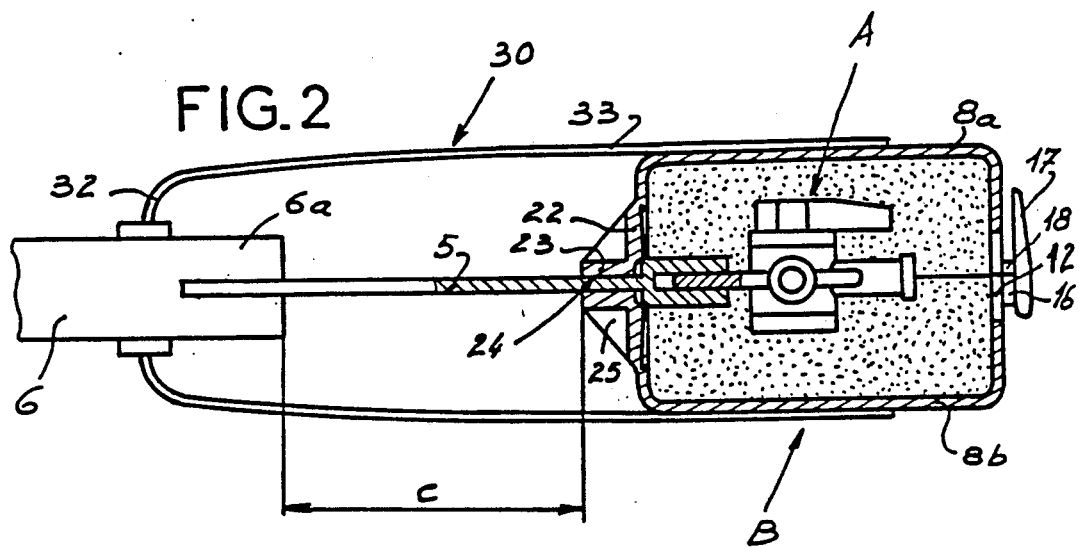
FIGS. 2 and 3 are transverse cross-sections of another embodiment of the protective structure when it is in the closed position and when it is in the open position, respectively.

The embodiment shown in FIGS. 2 and 3 differs from the above in that the two half-shells are associated with spring means that cause them to move down the panel 5 as soon as the locking means are activated in the unlocking direction. In the embodiment shown, the spring means comprises at least one U-shaped elastic strip 30 having a core 32 made integral with attachment body 6 of panel 5, and having free ends of arms 33 made integral with one or the other of the half-shells. By this, as soon as the locking systems are activated in the unlocking direction, arms 33 of the elastic strip naturally tend to spread apart, which has the effect of bringing together the free ends of these arms 33 in the direction of attachment body 6 and, at the same time, causing displacement in the same direction of slide 23 and the two half-shells 8a-8b, as shown in FIG. 3. In other words, unlocking of the closing means causes automatic retraction of the two half-shells 8a, 8b constituting a protective housing of connection site A.

In the embodiments shown above, panel 5 is not integral with the connection site A, but is made integral therewith by engaging a forked joint 34 provided at the front end of panel 5 integral with a panel 35 extending from connecting site A. Likewise, a rear edge of panel 5 is attached to attachment body 6 by engaging forked joint 6a of the body.

The assembly comprising the housing, the manifold, the panel, and the attachment body is made by casting synthetic material and is thus inexpensive, so that it can be discarded after one use.

From the foregoing, it is clear that the protective structure according to the invention allows excellent clearance of the connection site and hence facilitates the work of the caregivers, while eliminating any risk of injury.

I claim:

1. A protective structure for medical use having a connection site with at least one valve integral with an attachment panel, at least one tube being connected to the valve, and a housing slidably mounted on the panel, the housing including two half-shells made of a synthetic material, the half-shells being articulated by lengthwise rear walls, provided on lengthwise front walls with elastic closing means and provided with foam padding having depressions to accommodate the at least one valve and the at least one tube of the connection site, wherein the half-shells are articulated by independent, spaced hinges on thin lengthwise edges of a rear transverse wall integral with a slide and movably mounted on the panel, the length of the panel being at least equal to a distance that the slide must travel to achieve total clearance of the connection site by both half-shells in an open position.

2. The structure according to claim 1, wherein the two half-shells of the housing are connected to spring means which are able, when the housing opens, to move the two half-shells thereof on the panel in a direction of a rear end of the panel.

3. The structure according to claim 1, wherein the spring means is constituted by at least one elastic strip bent into a U shape, the strip having a core integral with a body affixed to an end of the panel opposite the connection site, and arms located one on each side of the panel attached at free ends to the two half-shells.

* * * * *